United States Patent
Afeyan et al.

(10) Patent No.: US 6,627,875 B2
(45) Date of Patent: Sep. 30, 2003

(54) TAILORED WAVEFORM/CHARGE REDUCTION MASS SPECTROMETRY

(75) Inventors: Noubar B. Afeyan, Lexington, MA (US); Scott McLuckey, West Lafayette, IN (US); Fred E. Regnier, West Lafayette, IN (US)

(73) Assignee: Beyond Genomics, Inc., Waltham, MA (US)

( * ) Notice: Subject to any disclaimer, the term of this patent is extended or adjusted under 35 U.S.C. 154(b) by 11 days.

(21) Appl. No.: 09/840,633

(22) Filed: Apr. 23, 2001

(65) Prior Publication Data

US 2002/0166958 A1 Nov. 14, 2002

(51) Int. Cl.[7] ............................................. B01D 59/44
(52) U.S. Cl. ..................................... 250/282; 250/291
(58) Field of Search ................................ 250/281–300, 250/423 R, 424–427

(56) References Cited

U.S. PATENT DOCUMENTS

| | | | | |
|---|---|---|---|---|
| 4,761,545 A | * | 8/1988 | Marshall et al. | 250/282 |
| 5,300,772 A | * | 4/1994 | Buttrill, Jr. | 250/282 |
| 5,324,939 A | * | 6/1994 | Louris et al. | 250/281 |
| 5,479,012 A | * | 12/1995 | Wells | 250/282 |
| 5,526,110 A | * | 6/1996 | Braymen | 250/252.1 |
| 5,569,917 A | * | 10/1996 | Buttrill, Jr. et al. | 250/282 |

FOREIGN PATENT DOCUMENTS

EP       626719 A2   4/1994

OTHER PUBLICATIONS

Scott A. McLuckey et al, Jul. 28–30, 1997, Proceedings from the First Joint Services Workshop on Biological Mass Spectroscopy, Baltimore, MD pp 28 (last paragraph).*

Dr. Alison Ashcroft, Feb. 22, 2001, "An Introduction to Mass Spectroscopy", The University of Leeds.*

McLuckey, S. et al. "Electrospray/Ion Trap Mass Spectrometry for the Detection and Identification of Organisms," *Proceedings from the First Joint Services Workshop on Biological Mass Spectrometry*, Baltimore, MD, Jul. 28–30, 1997, pp. 127–132.

McLuckey, S. et al. "Ion/Ion Proton–Transfer Kinetics: Implications for Analysis of Ions Derived from Electrospray of Protein Mixtures," *Anal. Chem.*, 1998, vol. 70, No. 6, pp. 1198–1202.

Hoffman, E. "Tandem Mass Spectrometry: a Primer," *Journal of Mass Spectrometry*, 1996, vol. 31, pp. 129–137.

Scalf, S. et al. "Charge Reduction Electrospray Mass Spectrometry," *Anal. Chem.*, 2000, vol. 72, No. 1, pp. 52–60.

Stephenson, Jr., et al. "Ion/Ion Reactions in the Gas Phase: Proton Transfer Reactions Involving Multiply–Charged Proteins," *Journal of the American Chemical Society*, 1996, vol. 118, No. 31, pp. 7390–7397.

(List continued on next page.)

*Primary Examiner*—John R. Lee
*Assistant Examiner*—Christopher M. Kalivoda
(74) *Attorney, Agent, or Firm*—Testa, Hurwitz & Thibeault, LLP

(57) ABSTRACT

The methods of the invention exploit the mass-to-charge ratio dependent motion of ions in an electrodynamic ion traps in synergy with a charge quenching process. In an electrodynamic ion trap, each mass-to-charge ratio is characterized by a unique set of frequencies of motion. Accordingly, by tailoring the time-varying electrical potential of the ion trap the invention controls which ions are allowed or retained in the ion trap and which ions are subjected to charge quenching reactions. Control of ion retention and charge quenching is used to improve sample throughput, dynamic mass range and signal discrimination in the mass spectrometry of multiply charged ions.

37 Claims, 4 Drawing Sheets

OTHER PUBLICATIONS

Stephenson, Jr., J. et al. "Ion/Ion Proton Transfer Reactions for Protein Mixture Analysis," *Anal. Chem.*, 1996, vol. 68, No. 22, pp. 4026–4032.

Stephenson, Jr., J. et al. "Ion/Ion Reactions for Oligopeptide Mixture Analysis: Application to Mixtures Comprised of 0.5–100 kDa Components," *J. Am. Soc. Mass. Spectrom*, 1996, vol. 9, pp. 585–596.

Stephenson, Jr., J. et al., "Ion–ion Proton Transfer Reactions of Bio–ions Involving Noncovalent Interactions: Holomyoglobin," *American Society for Mass Spectrometry*, 1997, vol. 8, pp. 637–644.

McLuckey, S., et al., "Ion/Molecule Reactions for Improved Effective Mass Resolution in Electrospray Mass Spectrometry" *Analytical Chemistry*, 1995, vol. 67, No. 14, pp. 2493–2497.

Marshall, A. G. "Milestones in Fourier transform ion cyclotron resonance mass spectrometry technique development," *International Journal of Mass Spectrometry*, 2000, vol. 200, pp. 331–356.

Stephenson, J. L. and McLuckey S.A., "Adaptation of the Paul Trap for study of the reaction of multiply charged cations with singly charged anions," *International Journal of Mass Spectrometry and Ion Processes*, 1997, vol. 162, pp. 89–106.

* cited by examiner-

TAILORED WAVEFORM/CHARGE REDUCTION MASS SPECTROMETRY

FIELD OF THE INVENTION

The invention relates generally to the field of mass spectrometry. In particular, the invention relates to a method and apparatus for electrodynamic ion trap mass spectrometry.

BACKGROUND OF THE INVENTION

Identification of molecular species by successive reactions in a mass spectrometer is known as "mass spectrometry/mass spectrometry," "multidimensional mass spectrometry," or more commonly "MS/MS," or "MS$^n$." In this process, an analyte ion usually decomposes spontaneously or is induced to fragment between stages of mass analysis. The process is executed by selecting an ion of specific mass-to-charge ratio (m/z) value and measuring the m/z value(s) of the fragment ions derived therefrom. Fragments of an ion are highly specific for the parent ion from which they are derived.

In a further exploitation of this process, a first generation fragment ion derived from a specific parent may be further fragmented and the second generation fragment ions mass analyzed. The number of ions available for analysis declines in each successive stage of fragmentation. The rate of decline depends upon the ion transmission characteristics of the mass spectrometer and the number and relative abundances of fragment ions in each stage. Sequential fragmentation reactions may be continued until the number of ions formed is below the detection level of the mass spectrometer being used. Fragmentation reactions constitute an important class of reactions in MS/MS. However, a variety of other types of reactions involving reactions of ions with molecules or with other ions can also be used between stages of mass analysis.

Electrospray ionization (ESI) is a process by which small droplets of liquid are sprayed from a charged capillary. These droplets are generally highly charged. As liquid evaporates from the sprayed droplets, they become smaller and the charge density increases. When the charge density is sufficiently high, droplets are further fragmented into smaller droplets by charge repulsion in the droplets. This cycle of evaporation and fragmentation by electrostatic repulsion continues until the charge density on the surface is sufficiently high that ions on the surface can desorb into the gas phase.

ESI is particularly effective in yielding multiply charged ions from species that can accommodate more than a single charge. Multiple charging is particularly common in proteins containing large numbers of free amine groups. For example, it would be possible in a protein containing 30 amine groups to exist as positive ions with a distribution of charge states in the range of +12 to +20, including species at every charge state within the range. The singly charged ion, however, is generally not observed because ions of such low charge state (z=1) are not typically formed via ESI. Because mass spectrometry separates ions on the basis of m/z, each of the charge states of the intact protein will produce a separate peak in a mass spectrometer. In the example of the protein described above, if the intact protein had a molecular weight of 20,000 Daltons (Da), ions would be measured at m/z=1000.00, m/z=1052.6, m/z=1111.1, m/z=1176.5, m/z=1250, m/z=1333.3, m/z=1428.6, m/z=1538.5, and m/z=1666.7. The molecular weight of the intact protein is obtained by using an algorithm that computes the probable molecular weight from the observed charge state distribution given by the peaks of the mass spectrum.

Since ESI produces multiple ions of varying charge states, analyzing mixtures of molecules is problematic, especially for mixtures of proteins. Even mixtures with a small number of species will produce so many ions that it is not possible to associate the various ions with the individual molecules from which they were derived. In addition, multiple charging compresses the "mass scale," that is, the distance between adjacent charge states on the m/z scale decreases with increasing charge, and further increase the difficulty of resolving molecules in a mixture.

Further, it is not uncommon for some of the charge states of molecules of different mass to have m/z values that are too similar to be resolved by the mass spectrometer. For example, an ion with a mass of 10,000 Da in a z=20 charge state will have substantially the same m/z value as an 5,000 Da ion in a z=10 charge state. Thus, the multiple charging phenomenon gives rise to the possibility that two molecules of different mass can give rise to ions with similar m/z values, thereby further complicating the analysis of a mixture of the molecules. For this reason, extensive efforts are usually undertaken to introduce relatively pure molecules, and in particular pure proteins, one molecular species at a time to an ESI ion source. These efforts ordinarily involve time-consuming off-line and on-line separations, severely limiting sample throughput.

The problem of multiple charging associated with ESI of mixtures has been addressed through charge quenching reactions. There are two general approaches by which charge quenching reactions can be effected. One approach involves mixing ions of opposite polarity in a region with minimal external electric or magnetic fields. This approach is exemplified by mixing ions of opposite polarity external to a mass spectrometer and sampling the charge quenched ions into the mass spectrometer for mass analysis. This approach constitutes a straightforward single stage mass spectrometry experiment and is not amenable to MS/MS or MS$^n$ procedures. The other general approach allows ions of opposite polarity to interact within combined electrostatic and magnetic fields or within an electrodynamic field, such as provided by electrodynamic ion traps. The latter approach allows for greater overlap in space of the oppositely charged ions.

In either general charge quenching approach, after ionization but before mass analysis, the charges of all ionic species are quenched to a single charge in the gas phase. Subsequent to charge quenching, the mixture is mass analyzed. This process substantially reduces the number of charged species in the gas phase before analysis and greatly simplifies the mass spectrum. Peaks in the spectrum appear at an m/z values equivalent to the molecular weight of the protein plus the mass of a proton.

The charge quenching process significantly improves the mixture analysis capabilities of electrospray. However, in many protein mixture analysis strategies, it is desirable to detect and quantify molecular species present at a wide range of concentrations. The concentration range over which mixture components can be measured is often referred to as "dynamic range." Thus, an accurate and reliable method of charge quenching over a large dynamic range is desirable.

What is needed is a mass spectrometry method and apparatus that improves the dynamic range, signal discrimination, and throughput of samples ionized by electrospray ionization.

SUMMARY OF THE INVENTION

The invention provides methods and apparatus that improve the sample throughput, dynamic mass range and signal discrimination in the mass spectrometry of multiply charged ions. The invention improves the dynamic range associated ESI of protein mixtures by as much as four orders of magnitude. The above advantages are of particular importance in the mass analysis of mixtures of molecules. In particular, the mass analysis of mixtures of biomolecules, including, but not limited to, proteins, peptides, carbohydrates, and oligonucleotides, can benefit from the invention.

The invention provides a method of mass spectrometry in which multiply charged ionic species are admitted into and/or retained in an electrodynamic ion trap in a mass to charge-ratio dependent (m/z-dependent) fashion and then partially charge quenched and subsequently mass analyzed. The procedure is repeated as a function of mass and allows for the measurement and quantification of multiple molecular species in a highly complex mixture. The methods of the invention provide for the detection of molecules of relatively low abundance in a mixture. For example, in one embodiment, ion trap accumulation times are varied to, for example, enhance the signals of low abundance molecular species ordinarily obscured by signals from much more abundant species.

In one aspect, the invention provides methods for analyzing a sample of molecules to obtain a mass spectrum of the sample. In particular, the methods of the invention are useful where an ion source produces a plurality of multiply charge ions from a sample. Such ion sources include, but are not limited to, electrospray ionization, laser desorption, and matrix assisted laser desorption ionization (MALDI) sources. The invention provides a charge quenching process that, in conjunction with a tailored waveform, serves to filter out ions of the same m/z value but with different mass. The methods of the invention can successively segregate subsets of ions from a mixture of multiply charged sample ions and then partially quench the charge state of the subset ions to produce a mass spectrum of the mixture with improved dynamic range and signal discrimination.

More specifically, a tailored waveform is used to segregate a subset of ions by applying the tailored waveform to an electrodynamic ion trap such that only ions in the subset are allowed into and/or are retained in the ion trap. That is, the tailored waveform allows only ions within select mass-to-charge ratio ranges into and/or to remain in the ion trap. In one embodiment, the subset of ions includes ions within mass-to-charge ratio (m/z) value ranges where the median values of the ranges are substantially the m/z values of the integer charge states of a select ion mass. For example, if the ion mass of interest is 10,000 Daltons (Da), the tailored waveform is created to allow and/or retain in the ion trap only m/z value ranges ("m/z ranges") with median values that correspond to the charge states of a 10,000 Da ion, e.g., median values of approximately m/z=10,000, m/z=5,000, m/z=3333.33, m/z=2,500 and so forth. The width of the m/z ranges are chosen, for example, based on the m/z values of the ions of interest, how the molecules are charged, the range of the m/z scale of interest, ion abundance, experimental protocol, instrumentation limitations, or investigator convenience. Preferable, the m/z ranges are chosen such that they do not significantly overlap. The subset ions allowed into and/or retained in the ion trap are then reacted with a quencher to lower the charge state of the ions in the ion trap. The quencher can be a neutral or have a charge, and can be an atom or a molecule. Preferably, the quencher is an ion of opposite polarity to that of the subset ions. After the ions in the ion trap have been reacted with a quencher, the resulting ions are released from the ion trap and a mass signal is determined for the highest mass-to-charge ratio ion by any suitable mass spectrometer or series of mass spectrometers. Suitable mass spectrometers include, but are not limited to, time-of-flight, quadrupole, Wein filter, magnetic sector, and electrostatic sector instruments.

In one embodiment, the ion of highest m/z value corresponds to the lowest charge state of the ion mass of interest ($z=1$). However, it is to be understood that depending on the reaction time and reaction rate between the ions and the quencher, the ions released from the ion trap may include, in addition to the highest m/z value ion, other lower order m/z ions, e.g., the second lowest ($z=2$), and/or the third lowest ($z=3$). According to certain embodiments of methods of the invention, after obtaining a mass signal for one ion mass of interest, the tailored waveform is varied to obtain a mass signal for at least one other ion mass of interest. In this manner, the methods of the invention can obtain a mass spectrum of a sample with improved dynamic range and signal discrimination.

In other embodiments, the invention also provides methods which increase dynamic mass range, signal discrimination, and/or signal-to-noise ratios, in an efficient manner conducive to high throughput sample analysis. In one embodiment, a tailored waveform is used to segregate a subset of ions by applying the waveform to an electrodynamic ion trap such that only ions in the subset are allowed into and/or are retained in the ion trap for an accumulation time. The subset of ions allowed into and/or retained in the ion trap are then reacted with a quencher to partially lower the charge state of the ions in the ion trap. After the ions in the ion trap have been reacted with the quencher, the ions are released from the ion trap and a mass signal is determined for the highest m/z value ion by any suitable mass spectrometer or series of mass spectrometers.

In one embodiment, if the mass signal intensity is too weak, the process is repeated with substantially the same tailored waveform for a longer accumulation time to increase the signal intensity. In another embodiment, if the mass signal intensity is too high, the process is repeated with substantially the same tailored waveform for a shorter accumulation time to decrease the signal intensity. In another embodiment, the accumulation time varies with the ion mass of interest based on, for example, the importance of the ion mass, analysis protocol, and/or known or suspected ion mass source. For example, some ion masses may only be of interest if they have a signal level above a certain threshold, such as those associated with certain food contaminants. Other ion masses may be of particular interest and warrant longer accumulation times, such as those corresponding to early markers for disease. Still other ion masses may be of little interest and warrant minimal accumulation times, such as those corresponding to known contaminants or experimental artifacts. In this manner the invention can obtain a mass spectrum of a sample with improved dynamic mass range, signal discrimination, and/or signal-to-noise ratios, in an efficient manner conducive to high throughput sample analysis.

In other embodiments, the invention provides methods of charge quenching in conjunction with the use of a tailored waveform. These embodiments can improve the distinction between ions of the same m/z value but different mass, while also improving dynamic mass range and signal discrimination. In one embodiment, a primary tailored waveform is used to segregate a first subset of ions by applying the primary tailored waveform to an electrodynamic ion trap such that only ions in a first subset are allowed into and/or are retained in the ion trap. The first subset of ions allowed in to and/or retained in the ion trap are then reacted with a quencher to partially lower the charge state of the ions in the ion trap. A secondary tailored waveform is then used to retain in the ion trap, a second subset of ions, which includes a subset of the first subset of ions. For example, the second subset of ions may include, for the ion mass of interest, only a certain charge state(s) of the charge states initially selected by the primary tailored waveform. This charge state(s) need not be the lowest charge state of the ion mass of interest and may comprise any combination of charge states.

For example, a secondary tailored waveform may retain both the lowest charge state and higher charge states. That is, a secondary tailored waveform could be generated to retain the lowest charge state ($z=1$), yet still retain select higher charge states which may contain a significant population of the ion mass of interest. The select higher charge states can be chosen, for example, based on the non-linear dependence of the reaction rate between ions and an ionic quencher of opposite polarity. After the application of the secondary tailored waveform, the ions are then released from the ion trap and a mass signal is determined for the highest m/z value ion by any suitable mass spectrometer or series of mass spectrometers. After obtaining a mass signal for one ion mass of interest, both the primary and secondary tailored waveforms may be varied to obtain a mass signal for at least one other ion mass of interest.

In another embodiment, the second subset of ions are also reacted with a quencher, which can be the same quencher as reacted with the first subset of ions or a different quencher. For example, the quencher reacted with the first subset of ions could be an ionic quencher of opposite polarity to take advantage of the non-linear dependence of ion—ion reaction rates on ion charge, while the quencher reacted with the second subset of ions could be a neutral species to avoid the non-linear dependence of ion—ion reaction rates. In another example, the quencher reacted with the second subset of ions could have a lower reaction rate than that reacted with the first subset of ions to prevent over-quenching the ion mass of interest (e.g., over-quenching to $z=0$).

In another aspect, the invention provides an apparatus including a waveform generator which is adapted to apply a tailored waveform having at least two gaps in frequency space to an ion trap. The waveform generator typically reacts in response to a control signal from a signal generator. The apparatus also includes a source of quencher ions in fluid communication with the ion trap.

The waveform generator can be any suitable device for applying a time varying electrical potential to an ion trap. The signal generator includes any suitable device that can generate control signals for the waveform generator. For example, a computer with appropriate hardware and software could serve as both a signal generator and a waveform generator. The source of quencher ions can be any suitable source that can be adapted to be in fluid communication with the ion trap. For example, a suitable source of neutral quencher species could be a gas cylinder. Suitable sources of ionic quenchers include, but are not limited to, electron ionization, discharge, and radioactive emission sources.

In one embodiment, the apparatus further includes several memory elements. The memory elements may be portions of the random access memory of a computer, and/or discreet memory elements of a computer, the signal generator, and/or the waveform generator. In one particular embodiment, the apparatus further includes: (1) a first memory element that stores an ion mass parameter; (2) a second memory element that contains a tailored waveform generator which determines a tailored waveform having at least two gaps in frequency space based on an ion mass parameter; (3) a third memory element that stores an accumulation time parameter; (4) a fourth memory element that contains a control signal generator which determines a control signal and the length of time the control signal is applied to the waveform generator based on an accumulation time parameter; and (5) a fifth memory element that contains a parameter generator which, in response to an update signal, changes the ion mass parameter and/or the accumulation time parameter.

In another embodiment, the apparatus further includes a source of ionized molecules in fluid communication with the ion trap. Any suitable ion source can be used including, but not limited to, electrospray, laser desorption, and MALDI ion sources. In another embodiment, the apparatus further comprises a mass spectrometer in fluid communication with the ion trap. Suitable mass spectrometers include, but are not limited to, time-of-flight, quadrupole, RF multipole, Wein filter, magnetic sector, and electrostatic sector instruments.

In another aspect, the invention provides an article of manufacture where the functionality of a method of the invention is embedded on a computer-readable program means, such as, but not limited to, a floppy disk, a hard disk, an optical disk, a magnetic tape, a PROM, an EPROM, CD-ROM, or DVD-ROM.

The foregoing and other features and advantages of the invention, as well as the invention itself, will be more fully understood from the description, drawings, and claims which follow.

DETAILED DESCRIPTION

The invention provides methods of mass spectrometry of particular benefit to the analysis of biological molecules and other complex samples. The invention provides methods that improve the mass analysis of samples which are ionized by sources that produce multiple ions of varying charge state. Ion sources which ionize a sample to produce multiple ions of varying charge state are referred to generally herein as "multi-charge state ion sources." Ion sources which can operate as multi-charge state ion sources include, but are not limited to, laser desorption, MALDI, and, in particular, electrospray ion sources.

Figure 1:
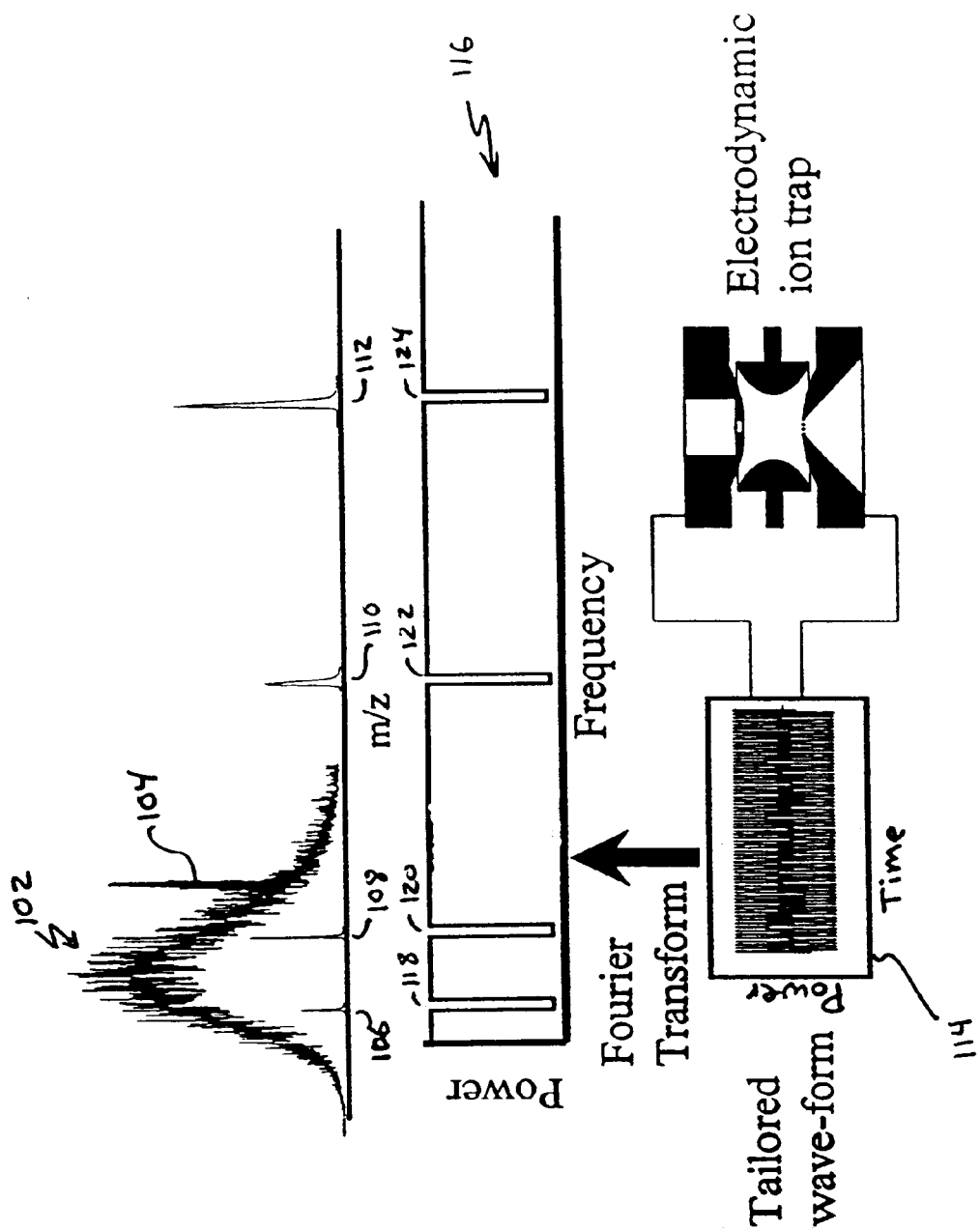
FIG. 1 is a pictorial overview of an embodiment of a process according to the invention.

Referring to FIG. 1, a pictorial overview of an embodiment of the invention is shown. In conventional mass spectrometry of a complex sample subjected to a multi-charge state ion source, the resulting mass spectrum 102 has overlapping mass signals from ions of different masses but similar m/z values. As a result, all but the most abundant mass-to-charge ratios (peaks in the spectrum) are obscured. Even where a m/z peak 104 is discernable, determination of the ion mass, or masses, associated with the m/z peak is ambiguous because the variety of ion charge states results in a high probability that more than one ion mass contributes to the m/z peak. In contrast, the methods of the invention substantially eliminate the obscuring effects associated with multi-charge state ion sources.

According to methods of the invention, only ions with m/z values in discreet ranges, accumulate in an ion trap, pictorially represented in FIG. 1 by a hypothetical mass signal 106, 108, 110, 112 for the associated m/z range. It should be noted that some of these mass signals, e.g., 110, 112 in the m/z range can correspond to low charge states that may not be produced by the ion source. In practice, a time-varying electrical potential based on a tailored waveform 114 (hereafter referred to as a "tailored waveform") is applied to an electrodynamic ion trap. The tailored waveform sets up electrodynamic fields that allow or retain in the ion trap only ions with m/z values within certain m/z ranges. The particular m/z ranges are established by the time-varying nature of the tailored waveform. The number of m/z ranges established is more easily seen from the frequency space representation of the tailored waveform 116. The frequency space representation 116 is readily obtained from the Fourier transform of the tailored waveform 114. As illustrated in FIG. 1, each m/z range typically appears as a gap 118, 120, 122, 124 in the frequency space representation of the tailored waveform. Accordingly, ions with m/z values that do not fall within the m/z ranges associated with these gaps in frequency space will not be allowed in and/or will be ejected from the ion trap.

Figure 2:
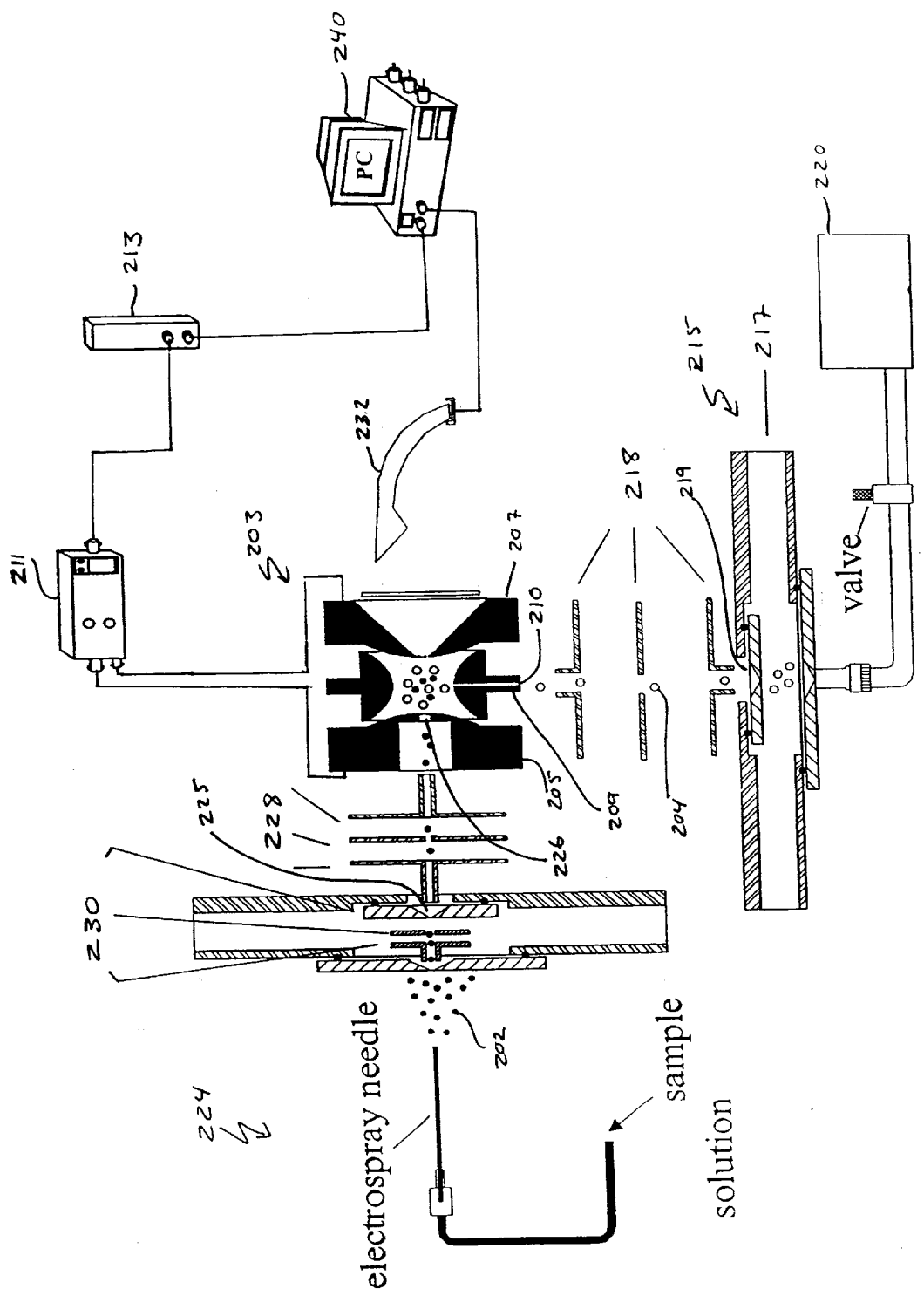
FIG. 2 is a schematic representation of an embodiment of an apparatus for practicing the methods of the invention.

Referring to FIG. 2, ions 202 allowed into and/or retained in an ion trap 203 are reacted with a quencher 204. Reaction between a quencher and an ion results in a lowering of the charge state of the ion. If, in its new charge state, the new m/z value of the ion remains within one of the ranges established by the tailored waveform, the ion is retained in the ion trap. Otherwise, the ion is ejected. The admission of ions into the trap and/or the reaction of ions with a quencher continues for an accumulation time. After the accumulation time, either all the ions remaining in the trap, or only those having m/z values in a certain m/z range(s) or above certain m/z values, are released from the ion trap and a mass signal determined. The mass signal can be determined using the electrodynamic ion trap as the mass analyzer or with another mass analyzer adapted to receive the ions released from the ion trap. Hypothetical examples of mass peaks observed with another mass analyzer after a charge quenching process according to one embodiment of the invention are illustrated in FIG. 1 as reference numerals 106, 108, 110, and 112.

Reaction of the quencher with the trapped ions can be performed in several ways. In one embodiment, the quencher is present in the ion trap prior to the introduction of ions into the trap. In another embodiment, the quencher is introduced into the trap substantially simultaneously with the ions. In another embodiment, the quencher is introduced into the ion trap after the ions are present. The quencher is reacted with the ions in the trap for a charge reduction period. The charge reduction period can be substantially the same as, shorter, or longer than the accumulation time. It should be realized that the charge reduction period is chosen based on, for example, the degree of charge reduction (quenching) desired, the charge reduction reaction rate, multi-charge state ion source characteristics, throughput criteria, and/or analysis convenience.

The quencher can be any suitable species for reducing the charge state of at least one ion mass allowed or retained in the electrodynamic ion trap. Suitable species include both ionic and neutral species. Ionic species should be of opposite charge of the ions to be quenched. When the quencher and the ions to be quenched are of opposite charge, the quenching reaction rate is typically much faster than for a neutral quencher species. In addition, the dependence of quenching reaction rate on ion charge state can be advantageously used.

More specifically, the capture rate between oppositely charge ionic species can be evaluated from the following equation:

$$k_c = v\pi \left[ \frac{z_1 z_2 e^2}{\mu v^2} \right]^2 \qquad (1)$$

where, in electrostatic units, $k_c$ is the rate constant for ion/ion capture, $v$ is the relative velocity, $z_1$ is the charge state of the ion, $Z_2$ is the charge state of the quencher, and $\mu$ is the reduced mass of the ion/quencher pair. Where the ions and quencher are ionic species of opposite polarity, the rate of charge reduction reactions depends upon the square of the charge states. Accordingly, high charge state ions are expected to react significantly faster than lower charge state ions.

In comparison, the reaction rate between an ionic and neutral species can be evaluated using the following equation:

$$k_{c(I/M)} = 2\pi z_1 \left[ \frac{\alpha}{\mu} \right]^{1/2} \qquad (2)$$

where $k_{C(I/M)}$ is the rate constant for ion/molecule capture, $z_1$ is the charge state of the ion, $\alpha$ is the polarizability of the quencher, and $\mu$ is the reduced mass of the ion/quencher pair. Here, where the quencher is a neutral species, the rate of charge reduction reactions depends linearly upon the ion charge state.

In one embodiment, where the ions of interest, i.e. those allowed into and/or retained in the ion trap, comprise cations, the quencher comprises a fluorocarbon anion, such as those derived from perfluoro-1,3-dimethylcyclohexane (PDCH). In one embodiment, where the ions of interest comprise protein cations formed by electrospray ionization and the quencher comprises a fluorocarbon anion, the charge reduction period is typically in the range from about 30 ms to about 350 ms.

The application of a tailored waveform and a charge quenching process can be conducted either in parallel or in series. In embodiments where the tailored waveform and charge quenching process occur in parallel, the tailored waveform is applied to the ion trap during the charge quenching process. In one embodiment, the tailored waveform is applied to eject ions with m/z values outside the m/z ranges established by the waveform. In this embodiment, no new ions are allowed in the ion trap by the tailored waveform, although ions with m/z values that are inside the m/z ranges established by the waveform are retained. Where the electrodynamic ion trap comprises a quadrupole ion trap 203 (see FIG. 2), the tailored waveform is applied such that substantially no ions are permitted to enter the trap through an entrance end-cap electrode 205 while ions with m/z values outside the m/z ranges established by the waveform are ejected through the end-cap electrodes (205 and 207). In another embodiment of parallel tailored waveform application and charge quenching, ions with m/z values inside the m/z ranges established by the waveform are permitted to enter the trap while those outside these ranges are ejected. The use of charge quenching in parallel with the application of the tailored waveform has a higher duty cycle and possibly greater dynamic range relative to a serial application of the waveform and charge quenching process.

In other embodiments, the tailored waveform is removed during introduction of the quencher into the trap and during the charge reduction period. As used here, when the tailored waveform is "removed," ions are substantially retained in the trap regardless of their m/z value. In other words, when reference is made to removal of the tailored waveform, it should be understood that electrical potentials are still applied to the ion trap which substantially retain the ions already therein. In one embodiment, where the tailored waveform application and charge quenching process occur in series, the tailored waveform is applied during ion accumulation to allow into the ion trap only ions with m/z values inside the m/z ranges established by the waveform. After ions have been allowed in the ion trap, the tailored waveform is removed and a quencher introduced for a charge reduction period. After the charge reduction period, the tailored waveform is reapplied and ions with m/z values outside the m/z ranges established by the waveform are ejected from the ion trap. It should be understood that in all embodiments of the serially practiced process that during reapplication of the tailored waveform, unreacted quencher species may be present in the ion trap.

In another embodiment where a tailored waveform application and charge quenching process are conducted in series, ions are first permitted to enter the ion trap regardless of their m/z values. A tailored waveform is then applied to eject all ions with m/z values outside the m/z ranges established by the waveform. Subsequently, the tailored waveform is removed and a quencher introduced for a charge reduction period. After the charge reduction period, the tailored waveform is reapplied and ions with m/z values outside the m/z ranges established by the waveform are ejected from the ion trap. In another embodiment, ions are first permitted to enter the ion trap regardless of their m/z values. A quencher is then introduced into the ion trap for a charge reduction period. After the charge reduction period, the tailored waveform is reapplied and ions with m/z values outside the m/z ranges established by the waveform are ejected from the ion trap.

The serial process of tailored waveform application followed by charge quenching can be repeated as often as desired to produce substantially low charge state ions. The serial process of tailored waveform application has several advantages relative to the parallel process. The use of a short charge quenching step prior to tailored waveform application may provide greater m/z dispersion of the ions. Further, where the quencher comprises ions of opposite charge to that of the ions of interest, the number of quencher ions admitted into the electrodynamic ion trap need not be carefully controlled. The presence of oppositely charged ions in an electrodynamic ion trap can affect the frequencies of ion motion in an uncontrolled fashion. For example, if there were too many quencher ions of charge opposite to the ions of interest, the ion frequencies would not match those calculated based on typical electrodynamic ion trap operating conditions. Thus, serial approach might be more readily implemented as a robust approach for mixture characterization.

An example illustrating an embodiment of the invention, where the ion mass of interest is 1000 Da, follows. A tailored waveform having two gaps in frequency space to allow into and retain in the ion trap only ions with m/z values inside m/z ranges substantially centered on m/z=500 and m/z=1000 is applied to one or more electrodes of an electrodynamic ion trap. For example, the m/z range may extend plus and minus 100 Da, plus and minus 50 Da, or even plus and minus 1 Da or less from the center m/z value. The m/z ranges are preferably chosen such that they do not significantly overlap. The tailored waveform selectively admits and/or retains only the ions with m/z values within the m/z ranges just mentioned. A quencher of oppositely charged ions reacts with the admitted ions either during the ion accumulation period or afterwards. The quencher induces charge quenching such that ions of m/z=500 and m/z=1000, other than singly charged ions (z=1), would shift in m/z value. All ions initially with values of m/z=500, but with a z value greater than 2, will shift to m/z values other than m/z=1000 and will be ejected.

For example, ions with a mass of 4000 Da and a charge state of z=4 would be allowed in the ion trap because their m/z value is 1000. Upon charge quenching to a lower charge state, for example, z=2, the m/z value of these 4000 Da ions shifts to 2000. As a result, when, or as, the tailored waveform is applied, these ions are ejected from the ion trap. In comparison, 1000 Da ions (the ions of interest) with a charge state of z=2 are allowed in the ion trap because their m/z values is 500. Upon charge quenching to z=1, these 1000 Da ions are still retained in the ion trap because their m/z values shifted to 1000. Thus, in this example, 4000 Da mass ions, which in the z=4 charge state masquerade as 1000 Da ions with z=1, are filtered out.

Further, if the 1000 Da ions are of relatively low abundance, the ion accumulation period is increased to accumulate a greater number of ions without also accumulating much more abundant ions of the same m/z value. Accumulation is generally more efficient when charge quenching is done during ion accumulation, i.e., where tailored waveform application and the charge quenching process are conducted in parallel.

Accordingly, a charge reduction period can be chosen such that those ions that remain in the ion trap are singly charged ions with a mass of either 500 or 1000 Da. A mass signal corresponding to a 1000 Da ion is then (measured) determined by, ejecting all ions in the ion trap and analyzing them with a suitable mass spectrometer. Alternatively, a mass signal is determined by ejecting only ions with masses sufficiently greater than 500 Da and directly measuring the ion signal. For example, the electric potentials applied to the electrodynamic ion trap can be adjusted so that ions with m/z values greater than 750 will "leak" out of the ion trap due to insufficient pseudopotential well depths.

More sophisticated tailored waveforms can be used for a mass of interest having many charge states. For a given set of electrodynamic ion trap operating conditions, the frequencies of motion in the ion trap for each of the possible ions formed from a molecule of a given mass can be calculated a priori. For example, mass-to-charge dependent frequencies of motion of ions in a pure oscillating quadrupolar field are:

$$\omega_{n,u} = (2n + \beta_u)\Omega/2 \qquad (3)$$

where u represents either the r-dimension (i.e., the radial plane of the ion trap) or the z-dimension (i.e., the inter-endcap dimension), n is a positive integer, $\Omega$ is the frequency of oscillation of the potential applied to the ion trap to effect ion storage, and $\beta_u$ is given approximately by:

$$\beta_u \cong (a_u + q_u^2/2)^{1/2} \qquad (4)$$

The $a_u$ parameter is given by:

$$a_u = (\text{constant})eU/(mr_0^2 \Omega^2) \qquad (5)$$

and the $q_u$ parameter is given by:

$$q_u = (\text{constant})eV/(mr_0^2 \Omega^2) \qquad (6)$$

where the constants depend upon the specific operating mode of the ion trap, U is the DC potential between the electrodes (usually=0), V is the amplitude of the radio-frequency potential used to trap the ions, $r_0$ is the radius of the ring electrode, and m/e is the mass-to-charge ratio of the ion. By far, the most important frequencies of motion are the so-called fundamental secular frequencies of motion defined by the condition of n=0. The application of a single frequency wave-form to the end-cap electrodes can result in the z-dimension acceleration of ions of a particular mass-to-charge ratio. The use of multiple frequencies can effect the simultaneous acceleration of ions of multiple mass-to-charge ratios. Judicious selection of the amplitudes and frequencies of the components of a tailored wave-form applied to the end-cap electrodes allows for a high degree of flexibility in selecting which ions are ejected from the ion trap and which ions are retained. A time-domain trace of the applied wave-form can appear to be quite complex when various ions are being ejected from the ion trap. A Fourier transformation of the time-domain trace yields the frequency-domain spectrum of the applied wave-form.

It should be realized, however, that ion retention and resonance ejection of high m/z value ions in an electrodynamic ion trap can be affected by the presence of an ion cloud of opposite polarity in the center of the ion trap with much higher total charge. For example, high m/z ions can be trapped, i.e., retained in the ion trap, by an electric field created by an ionic quencher cloud of opposite polarity when the trapping potential created by the electrodynamic ion trap is itself insufficient to do so. This can create a situation where an ion trap traps quencher ions which, in turn, trap high m/z ions. This phenomenon can be exploited to retain ions of higher m/z in the ion trap than might otherwise be possible. Another effect due to the presence of an ion cloud of opposite polarity and much higher total charge in the center of the trap is that the ion cloud of opposite polarity can interfere with resonance ejection, and as a result, the mass analysis of high m/z ions. For this reason, it is desirable to eject ionic quencher species prior to resonance ejection of the ions of interest.

Although equations 3 and 4 indicate that the tailored waveform can be chosen to allow or retain in the ion trap a precise m/z value or values, in practice, the tailored waveform actually allows or retains in the ion trap a range of m/z values about any one value. This occurs for both practical and analytical reasons. For example, imperfections in actual time-varying power sources place a practical limit on how precise or narrow a range of m/z values can be established by tailored waveform. In addition, the way a molecule is charged can provide a range, or ranges, of m/z values. More specifically, molecules can be charged by different means, such as proton gain or loss, and/or electron gain or loss and combinations thereof. For example, a 1000 Da molecule could acquire a +2 charge state by gaining two protons, gaining of one proton and losing of one electron, or losing of two electrons. Hence, in this example, the 1000 Da mass molecule with z=2 could appear at m/z=1002/2=501, m/z=1001/2=500.5, and/or m/z=1000/2=500.

It should be realized that throughout the discussion of ions of various charge states that the ion masses given or associated with an m/z value are generally for ions where charge is obtained by electron gain or loss. This convention is purely for the sake of convenience as the methods and apparatus of the invention are applicable to any ion, no matter how charge is created. Thus, where charging includes proton gain or loss, adjacent charge states of a base molecule mass will vary by the mass of a proton. Similarly, where charging includes gain or loss of a functional group, adjacent charge states of a base molecule mass will vary by the mass of the functional group.

Figure 3:
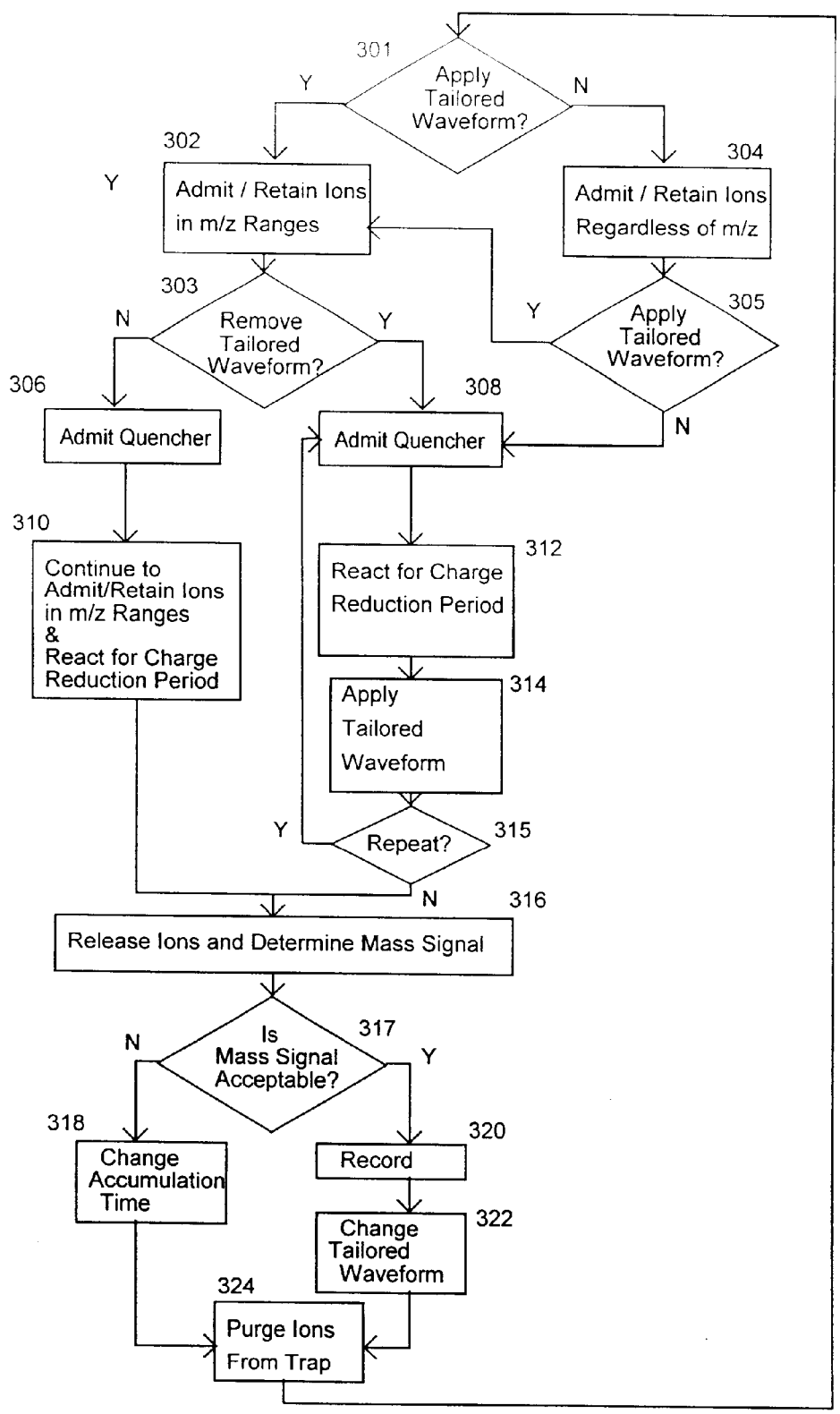
FIG. 3 is a flow diagram showing various embodiments of methods of the invention.

Referring to FIG. 3, various embodiments of methods of the invention are illustrated. The practice of these methods as discussed below is also in the context of the apparatus of FIG. 2. Further, the illustrative example is the analysis of a sample of a mixture of molecules that is ionized with an electrospray ion source. It is to be understood that the specifics of the sample, the multi-charge state ion source, and the electrodynamic ion trap are not central to the methods of the invention, but are discussed herein to better illustrate these methods. An analysis begins by admitting ions into the electrodynamic ion trap.

In one embodiment, a tailored waveform is initially applied to an ion trap thereby allowing only ions with m/z values within the m/z ranges established by the tailored waveform to enter and remain in the ion trap ("YES" to query 301). Ions within the m/z ranges established by the tailored waveform are admitted and retained in the ion trap for an accumulation time 302, segregating a subset of the ions, based on m/z values, from the plurality of ions produced by the ion source. A quencher is admitted into the ion trap to reduce the charge state of the ions therein (step 306 or 308). In one embodiment, where the ion trap is a quadrupole ion trap, the quencher is admitted through a small hole in the ring electrode 209 of the trap.

As discussed above, the quenching process can be conducted with the tailored waveform removed from the ion trap ("serial approach," "YES" to query 303), or applied to the ion trap ("parallel approach," "NO" to query 303). In embodiments of the serial approach, the quencher is reacted with the ions in the ion trap for a charge reduction period 312 and ions are retained in the ion trap substantially regardless of their m/z values. After the charge reduction period, the tailored waveform is reapplied thereby ejecting ions from the trap with m/z values outside the m/z ranges established by the waveform 314. It should be realized that depending on, for example, the charge reduction period, quenching reaction rate, ion number density and quencher number density, ion-quencher reactions may still take place during the reapplication of the tailored waveform 314. As discussed above, the serial application of the charge quenching process and tailored waveform can be repeated ("YES" to query 315) to, for example, further accumulate ions with m/z valves in the m/z range(s) of interest. Subsequent to reapplication of the tailored waveform, and any repetition cycles, all the ions remaining in the ion trap, or a subset of the ions remaining in the trap, are released and a mass signal determined 316.

In embodiments of the parallel approach ("NO" to query 303), the tailored waveform is not removed during the charge quenching process. In one embodiment of the parallel approach, the tailored waveform continues to admit and retain ions with m/z values substantially within the m/z ranges established by the tailored waveform as a quencher is introduced. The quencher reacts with the trapped ions for a charge reduction period 310. In another embodiment, the tailored waveform is applied such that no new ions are admitted into the ion trap, but only ions with m/z values substantially within the m/z ranges established by the tailored waveform are retained. Accordingly, as a quencher reacts with the trapped ions for a charge reduction period 310 certain "quenched" ions may be ejected. In one embodiment where the ion trap comprises a quadrupole ion trap, new ions are not admitted into the ion trap and ions with m/z values substantially within the m/z ranges established by the waveform are retained by application of the tailored waveform to one or both of the end-cap electrodes 205 and 207.

In the parallel application of the tailored waveform and charge quenching process 310, the accumulation time and charge reduction period may be of substantially the same, or different, duration. The duration of the accumulation time and charge reduction period are determined based on, for example, space charge, multi-charge state ion source characteristics, charge reduction reaction rate, the degree of charge reduction (quenching) desired, ion number density, quencher number density, the importance of the ion mass, analysis protocol, known or suspected ion mass source, throughput criteria, and/or analysis convenience. Subsequent to the charge reduction period or accumulation time, all the ions remaining in the trap, or a subset of the ions remaining in the trap, are released and a mass signal determined 316.

In either the parallel or serial approach, the ions released from the ion trap after charge quenching may be detected directly or subjected to further mass analysis to determine a mass signal. The released ions may be directly detected with, for example, a channeltron electron multiplier, a discrete dynode electron multiplier, a CCD, electron multiplier, Faraday cup, Daly detector, or simply a conductive plate electrically connected to an ammeter, to determine a mass signal. The use of a tailored waveform in conjunction with a charge quenching process results in an ion signal for the released ions that corresponds to an ion mass. The degree of correspondence between the measured ion signal and the abundance and/or presence of the ion mass depends, for example, on the extent of charge quenching and whether all or a subset of ions are released and detected from the ion trap. Alternatively, the released ions may be further mass analyzed with, for example, a time-of-flight, a quadrupole, a magnetic sector, Wein filter, or an electrostatic mass spectrometer to determine a mass signal. In embodiments where the released ions are further mass analyzed, the invention provides a front end mass spectrometer that increases the dispersion and dynamic range of the second mass spectrometer. Accordingly, in these embodiments, the invention provides a MS/MS or MS$^n$ system.

A mass signal is determined based on the measured ion signal for the released ions. The mass associated with the mass signal is determined based on the m/z ranges established by the tailored waveform last applied to the ion trap prior to ion release. For example, where the tailored waveform is chosen such that the median values of the m/z ranges established include the integer charge states of a mass of interest, the released ion signal corresponds to the mass of interest. The degree of correspondence depends, for example, on the extent of charge quenching and whether all or a subset of ions are released and detected from the trap. Where the released ion signal comprises ions in a low charge state(s), the correspondence is high and generally increases as the proportion of released ions in the z=1 charge state increases. Accordingly, the mass signal for ions with the highest m/z is generally determined.

It should be understood, however, that the invention can determine a mass signal for ions other than those with the highest m/z allowed and/or retained in the ion trap. For example, where a significant proportion of an ion signal is found, or predicted, for an m/z value with a charge state higher than z=1, yet ions with z=1 charge state where allowed and/or retained in the ion trap, a mass signal can be determined for the ions with the m/z value corresponding to the higher charge state(s). In another example, where the released ions are subjected to further mass analysis, the fragmentation pattern of a specific m/z value, or values, can be used to identify the ion mass to associate with an ion signal(s).

The association of an ion signal of released ions with a mass to yield a mass signal is referred to herein as "binning" The mass, or range of masses, associated with measured the ion signal is referred to herein as a mass "bin." A display of a range of molecule masses of a sample, i.e. a mass spectrum, can be generated using methods of the invention by binning over a mass range, that is, molecules within suitably narrow mass ranges established by a tailored waveform can be detected through the successive use of the charge quenching process described above whereby a substantially unique tailored waveform is chosen for each mass bin so that a substantially unique mass, or range of masses, is associated with each mass bin.

A mass spectrum of a mixture of molecular species ionized with a multi-charge state ion source may be obtained as follows. For example, assume a mass spectrum is desired over the m/z scale range of 50 Da to 500,000 Da. Using the methods of the invention a tailored waveform is applied to an ion trap to retain and/or admit only ions with m/z values inside m/z ranges substantially centered on m/z values that correspond to the charge states of 50 Da molecules and with a width of 100 Da. Ions are accumulated, charge quenched, trapped ions released, and an ion signal measured. The measured ion signal is then associated with 50 Da mass molecules. That is, the measured ion signal is put into the 50 Da mass bin. Accordingly, the measured ion signal intensity is representative of the 50 Da molecules present in the mixture.

To generate a mass spectrum, the tailored waveform is changed to admit and/or retain ions with m/z values that correspond to the charge states of another molecular mass. In one embodiment, the tailored waveform is changed so that the next set of center values of the next set of m/z ranges are the previous corresponding center values plus the width of the previous m/z range. In the example above, the tailored waveform is thus changed to retain and/or admit only ions with m/z values inside m/z ranges substantially centered on m/z values that correspond to the charge states of 150 Da molecules. The process of ion accumulation, charge quenching, trapped ion release, and an ion signal measurement is repeated according to the methods of the invention to determine a mass signal for the 150 Da mass bin. Accordingly, to generate a mass spectrum for the m/z scale range from 50 Da to 500,000 Da, the tailored waveform is systematically changed to step the center values of the m/z ranges in 100 Da increments until the upper limit of the m/z scale range is reached. It is to be understood however, that the centers of the m/z ranges do not need to be stepped sequentially, but rather can be stepped in any order, e.g. 50 Da, to 50,050 Da, to 250 Da. In this manner a mass spectrum of molecules ionized by a multi-charge state ion source can be obtained with improved sample throughput, dynamic mass range and signal discrimination.

In another embodiment, the center of the m/z range is stepped by an amount that is significantly less than the width of the m/z range; hence, the mass ranges of the mass bins overlap. In these embodiment, using techniques known to the art, a mass signal can be determined from the difference between adjacent overlapping mass bins to generate a new mass bin that is narrower than either of the overlapping bins. It should be further, realized that the mass bins chosen, i.e., the masses for which a mass signal is determined, need not cover the entire range of the m/z scale. For example, the range of the m/z scale may be from 500 Da to 200,000 Da but the masses of interest correspond to disease markers with masses of 500 Da, 25,000 Da and 150,000 Da; accordingly, the methods of the invention may be used to determine mass signals only for mass bins centered substantially on 500 Da, 25,000 Da and 150,000 Da. Hence, further analysis, e.g. determination of mass signals for other mass bins, may be undertaken only if a sufficient mass signal intensity is appears in one or more of the mass bins associated with the disease marker masses.

In one embodiment, the measured ion signals are normalized when determining the mass signals. In one embodiment, the mass signals determined from normalized ion signals are used to quantify the relative abundances of molecular masses in the sample under analysis. The ion signals may be normalized for, for example, ion accumulation time, charge reduction period, charge reduction reaction rate, ion number density, and/or quencher number density.

Referring to FIG. 3, in a preferred embodiment, after a mass signal is determined for a tailored waveform, the mass signal is recorded 320, the tailored waveform is changed 318, ions are purges from the trap 324, and at least one other mass signal is determined corresponding to the mass range established by the other waveform. By systematically changing the tailored waveform, and binning the measured ion signal into successive mass bins, a mass spectrum of a sample under analysis can be obtained.

In other embodiments, the mass signal is recorded 320 only if the mass signal is considered acceptable ("YES" to query 317). Whether a mass signal is acceptable is determined, for example, based on the mass signal intensity, the signal-to-noise ratio for the mass signal, the mass of interest, the importance of the ion mass, analysis protocol, known or suspected ion mass sources, throughput criteria, and/or analysis convenience. In embodiments where the released ions are further mass analyzed, whether a mass signal is acceptable (query 317) may be based on one, a subset or all of the ion signals observed, or predicted to be observable, after further mass analysis.

In cases where the mass signal is not acceptable ("NO" to query 317), the mass signal is not recorded, the ion accumulation time is changed 318, ions are purged from the ion source 324, and the mass signal is redetermined using the new accumulation time. The accumulation time which is changed can be any of the accumulation times associated with the invention, individually or in combination. For example, in a serial approach, the accumulation time associated with step 302, step 314, or both may be changed. In these embodiments, an accumulation time may be increased to increase the signal intensity of the mass signal, or an accumulation time may be decreased to shorten the analysis time (e.g., to increase throughput). More specifically, in cases where molecules are in high abundance within a certain mass bin, a relatively short ion accumulation time can be sufficient to provide good ion detection statistics. Conversely, where molecules are of low abundance for a given mass bin, the ion accumulation time can be extended to improve ion detection statistics. A mass spectrum with good ion detection statistics can then efficiently be obtained with the methods of the invention by systematically changing the tailored waveform, varying the ion accumulation time, and binning the measured ion signal into successive mass bins.

Ion accumulation times in electrodynamic ion traps typically range from about 100 $\mu$s to about 1 s (there is no fundamental upper limit to ion accumulation). This range extends over 4 orders of magnitude and provides significant advantages for dynamic range extension in mixture analysis.

In one embodiment where the ions of interest comprise protein cations formed by electrospray ionization, ion accumulation times typically have values in the range from about 0.02 s to about 0.2 s. The measured ion signals may also be normalized for ion accumulation time when determining the mass signals and the resulting the mass signals further used to quantify the relative abundances of molecular masses in the mixture sample under analysis.

In other embodiments, where a mass signal is not acceptable ("NO" to query 317), the quencher is changed, ions are purged from the ion source 324, and the mass signal is redetermined using the new quencher. In other embodiments, where a mass signal is not acceptable ("NO" to query 317), the charge reduction period is changed, ions are purged from the ion source 324, and the mass signal is redetermined using the new charge reduction period. For example, the charge reduction period could be shortened to prevent over-quenching the ions of interest (e.g., to the z=0 charge state).

Referring again to FIG. 3, in another embodiment, no tailored waveform is initially applied to the ion trap ("NO" to query 301). In embodiments where no tailored waveform is initially applied to the ion trap ("NO" to query 301), a quencher may be admitted to the ion trap prior to application of a tailored waveform ("NO" to query 305 and step 308). The quencher is then reacted with the ions in the ion trap for a charge reduction period 312 and ions are retained in the ion trap substantially regardless of their m/z values. After the charge reduction period, the tailored waveform is reapplied to eject ions from the ion trap with m/z values outside the m/z ranges established by the tailored waveform 314. Subsequent to reapplication of the tailored waveform, all the ions remaining in the trap, or a subset of the ions remaining in the trap, are released and a mass signal determined 316. Accordingly, ions are initially admitted into and retained in the trap regardless of their m/z values 304 for an accumulation time. A tailored waveform may then be applied to eject ions from the ion trap with m/z values outside the m/z ranges established by the tailored waveform ("YES" to query 305 and step 302). Subsequently, a quencher is admitted into the ion trap for reducing the charge state of the ions therein (step 306 or 308). As discussed above, the quenching process can be conducted with the tailored waveform removed from the ion trap ("serial approach," "YES" to query 303), or applied to the trap ("parallel approach," "NO" to query 303).

In embodiments of the serial approach, the tailored waveform is removed ("YES" to query 303), the quencher is reacted with the ions in the ion trap for a charge reduction period 312 and ions are retained in the ion trap substantially regardless of their m/z values. After the charge reduction period, the tailored waveform is reapplied to eject ions from the ion trap with m/z values outside the m/z ranges established by the tailored waveform 314. Subsequent to reapplication of the tailored waveform, all the ions remaining in the trap, or a subset of the ions remaining in the trap, are released and a mass signal determined 316.

In embodiments of the parallel approach ("NO" to query 303), the tailored waveform is not removed during the quenching process and ions are admitted into and/or retained in the ion trap as the quencher is admitted. As discussed above, in the parallel application of the tailored waveform and charge quenching process 310, the accumulation time and charge reduction period may be of substantially the same or different duration. Subsequent to the charge reduction period and/or accumulation time, all the ions remaining in the trap, or a subset of the ions remaining in the trap, are released and a mass signal determined 316.

Figure 4:
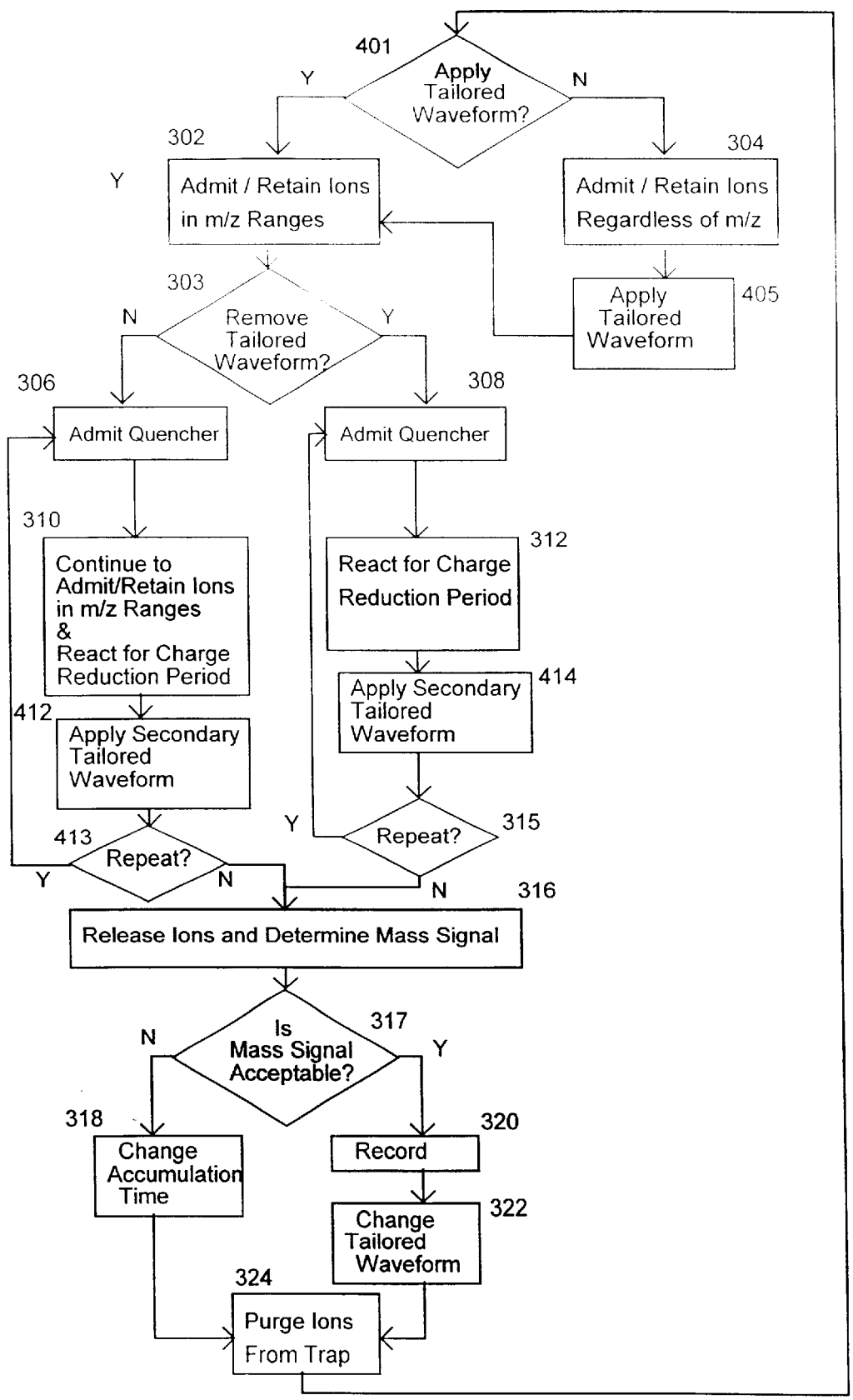
FIG. 4 is a flow diagram showing various embodiments of methods of the invention.

The invention also provides another method of charge quenching in conjunction with the use of a tailored waveform that can improve the discrimination between ions of the same m/z value but different mass, while also improving dynamic mass range and signal discrimination. Referring to FIG. 4, in one embodiment, a primary tailored waveform is used to segregate a first subset of ions by applying the primary tailored waveform to an electrodynamic ion trap such that only ions in a first subset are allowed into and/or are retained in the ion trap. The primary tailored waveform can be applied initially ("YES" to query 401 and step 302), or subsequent to initial filling of the ion trap ("NO" to query 401 and step 405). The first subset of ions allowed into and/or retained in the ion trap are then reacted with a quencher to partially lower the charge state of the ions in the trap, step 306 or 308.

As discussed previously, the tailored waveform can be applied in series or in parallel with the change quenching process. In either the parallel or serial approach, a secondary tailored waveform is applied, step 412 or 414, to retain in the ion trap a second subset of ions which includes a subset of the first subset of ions. For example, the second subset of ions may include, for the ion mass of interest, only a certain charge state(s) of the charge states initially selected by the primary tailored waveform. This charge state(s) need not be the lowest charge state of the ion mass of interest and may comprise any combination of charge states. For example, the primary waveform may retain only higher charge states while the secondary tailored waveform may retain the lowest charge state and the lower of the higher charge states. Such a secondary waveform could retain the lowest charge state (z=1) yet still retain select higher charges states which may contain a significant population of the ion mass of interest. The select higher charge states can be chosen based on, for example, the non-linear dependence of the reaction rate between ions and an ionic quencher of opposite polarity, the characteristics of the multi-charge state ion source, or the known or suspected presence of interfering ion masses.

The serial or parallel approach of charge quenching and application of a tailored waveform may be repeated ("YES" to query 315 or 413). Upon repetition, substantially the same secondary tailored waveform may be applied or another, e.g., tertiary, tailored waveform may be used. For example, if a tertiary tailored new waveform is applied, it retains in the ion trap a third subset of ions, which comprises a subset of the second subset of ions retained in the ion trap. After the application of the secondary, or tertiary, or subsequent and final) tailored waveform, the ions are then released from the ion trap and a mass signal is determined 316. In one embodiment, after obtaining a mass signal for one ion mass of interest, both the primary and secondary tailored waveforms are varied to obtain a mass signal for at least one other ion mass of interest 322. A mass spectrum can then be obtained with the methods of the invention by systematically changing the primary tailored waveform, and binning the measured ion signal into successive mass bins.

In another embodiment, the mass signal is recorded 320 only if the mass signal is considered acceptable ("YES" to query 317). Where the mass signal is not acceptable ("NO" to query 317), the mass signal is not recorded, the ion accumulation time is changed 318, ions are purged from the ion source 324, and a mass signal is redetermined using the new accumulation time. Any of the accumulation times associated with the practice of the invention may be changed. In the serial approach, for example, the accumulation time that is changed can be that step 302, that of step 314, or both. In other embodiments, where the mass signal is not acceptable ("NO" to query 317), the quencher is changed, ions are purged from the ion source 324, and the mass signal is redetermined using the new quencher. In other embodiments, where the mass signal is not acceptable ("NO" to query 317), the charge reduction period is changed, ions are purged from the ion source 324, and the mass signal is redetermined using the new charge reduction period. For example, the charge reduction period could be shortened to prevent over-quenching the ions of interest (e.g., to the z=0 charge state). A mass spectrum with acceptable mass signals can then efficiently be obtained with the methods of the invention by systematically changing the tailored waveform, varying the charge reduction period, and binning the measured ion signal into successive mass bins.

In another aspect, the invention provides an apparatus. Referring again to FIG. 2, one embodiment of an apparatus adapted to practice the invention is shown. The apparatus includes an electrodynamic ion trap 203 in electrical communication with a waveform generator 211. In one embodiment, as shown in FIG. 2, the electrodynamic ion trap includes a quadrupole ion trap having an entrance end-cap electrode 205, an exit end-cap electrode 207, and a ring electrode 209. In one embodiment, where the ion trap comprises a quadrupole ion trap, the entrance end-cap electrode 205 is modified for admission of ions formed external to the ion trap. An apparatus according to the invention, however, can comprise any ion trap, including, but not limited to electrodynamic, electrostatic, and combined electrostatic/magnetic ion traps, the latter of which is sometimes referred to as an ion cyclotron resonance (ICR) ion trap. The waveform generator 211 is adapted to apply a time-vary electrical potential that includes a tailored waveform having at least two gaps in frequency space to the electrodynamic ion trap 203 in response to a control signal from a signal generator 213. The signal generator 213 can include any suitable device that can generate control signals for the waveform generator 211. For example, a computer with appropriate hardware and software could serve as a signal generator 213.

The apparatus of the invention further includes a source of quencher ions 215 in fluid communication with the electrodynamic ion trap 203. In one embodiment, where the electrodynamic ion trap comprises a quadrupole ion trap, the quencher ions enter the ion trap through a hole 210 in the ring electrode 209. In one embodiment, the quencher species include neutral species and the source of quencher neutrals is a gas reservoir in fluid communication with the ion trap. In other embodiments, the quencher species include ionic species and the source of quencher ions is an appropriate ion source, such as, among others, electron ionization, discharge, and radioactive emission sources.

In one embodiment, illustrated in FIG. 2, the quencher source includes a glow discharge ion source 217. The ion trap 203 is situated such that there is a line of sight from the exit aperture 219 of the glow discharge ion source 217 to the hole 210 in the ring electrode 209. In one embodiment, the hole has a diameter in the range from about 2 mm to about 4 mm. An ion lens 218 may be mounted off the glow discharge ion source 217 to facilitate quencher ion transport to the ring electrode 209. In a preferred embodiment, helium is admitted into a vacuum system which houses the electrodynamic ion trap to a total pressure of about 1 mtorr and quencher anions are formed by sampling the headspace vapors of a perfluorocarbon such as perfluoro-1,3-dimethylcyclohexane (PDCH), contained in a reservoir 220, into the glow discharge operated at 800 mtorr.

The glow discharge ion source may be pulsed. The output of a pulser (not shown) is connected to the anode of the glow discharge ion source. The pulser acts as a fast switch which alternates between a voltage sufficient to strike a discharge and ground. This arrangement allows for independent control of ion 202 and quencher ion 204 accumulation in the ion trap 203.

In another embodiment, the apparatus further includes a source of ionized molecules 224 in fluid communication with the electrodynamic ion trap 203. Ions typically are admitted axially into the electrodynamic ion trap from the ion source. Any suitable ion source can be used including, but not limited to, electrospray, laser desorption, and MALDI ion sources. In addition, the ion source may further include a device which delivers samples to the ion source, such as by capillary electrophoresis, gas phase chromatography, and liquid phase chromatography. As illustrated in FIG. 2, the ion source 224 comprises an electrospray ion source. The ion trap 203 is situated such that there is a line of sight from the exit aperture 225 of the electrospray ion source 224 to a hole 226 in the entrance end-cap electrode 205. Interface lenses 230 and an ion lens 228 are mounted off the electrospray ion source to facilitate ion transport to the entrance end-cap electrode 205.

As shown in FIG. 2, the apparatus may further include an ion detector 232 or a mass spectrometer(s) (not shown) in fluid communication with the electrodynamic ion trap. Suitable detectors include, but are not limited to, channeltron electron multipliers, discrete dynode electron multipliers, CCDs, faraday cups, or simply a conductive plate electrically connected to an ammeter. Suitable mass spectrometers include, but are not limited to, time-of-flight, quadrupole, Wein filter, magnetic sector, and electrostatic sector instruments.

The apparatus may further include a several memory elements. In one particular embodiment, the apparatus further includes: (1) a first memory element that stores an ion mass parameter; (2) a second memory element that contains a tailored waveform generator that determines a tailored waveform having at least two gaps in frequency space based on an ion mass parameter; (3) a third memory element that stores an accumulation time parameter; (4) a fourth memory element that contains a control signal generator that determines a control signal and the length of time the signal is applied to the waveform generator based on an accumulation time parameter; and (5) a fifth memory element that contains a parameter generator which in response to an update signal, changes the ion mass parameter and/or the accumulation time parameter.

In another embodiment, the apparatus further includes a sixth memory element that stores a charge reduction period parameter which is accessed by a quencher source control signal generator. The quencher source control signal, which may be contained in a seventh memory element, provides a quencher control signal which determines the length of time a quencher is admitted into or retained in the electrodynamic ion trap. The quencher control signal may be used to control the tailored waveform applied to the ion trap which retains the quencher in the trap to the quencher control signal may also be used to control the quencher source which generates the quencher species, and/or any other elements that facilitate the transport of the quencher from the quencher source to the ion trap.

The memory elements may be portions of the random access memory of a computer, and/or discreet memory elements of a computer, a signal generator, or a waveform generator. As illustrated in FIG. 2, the memory elements include portions of the random access memory of a computer, and/or discreet memory elements of a computer 240. The memory elements described herein may be discreet memory elements that receive data and are accessed by the tailored waveform generator, the control signal generator, and the parameter generator. Alternately, the memory elements may refer to a portion of random access memory which is set aside to store the data transmitted thereto.

In some embodiments, the functionality of the methods described above may be implemented as software on a general purpose computer. The computer may be separate from, detachable from, or integrated into an electrodynamic ion trap. In addition, such a program may set aside portions of a computer's random access memory to provide control logic that affects tailored waveform generation, parameter selection, mass signal recording, and the operations with and on the data stored in the memory elements. In such an embodiment, the program may be written in any one of a number of high-level languages, such as FORTRAN, PASCAL, C, C++, or BASIC. Further, the program may be written in a script, macro, or functionality embedded in commercially available software, such as EXCEL or VISUAL BASIC. Additionally, the software could be implemented in an assembly language directed to a microprocessor resident on a computer. For example, the software could be implemented in Intel 80×86 assembly language if it were configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of analyzing a sample of molecules comprising the steps of:
 (a) using a tailored waveform having at least two gaps in frequency space to segregate a subset of ionized molecules from a plurality of ionized molecules;
 (b) reacting the subset of ionized molecules with a quencher for a charge reduction period to reduce the charge state of ionized molecules in the subset of ionized molecules;
 (c) determining a mass signal for the ionized molecules having the highest mass to charge ratio resulting from step (b); and
 (d) repeating steps (a)–(c) for at least another tailored waveform having a different at least two gaps in frequency space to define a mass spectrum.

2. The method of claim 1 further comprising the steps of:
 using the tailored waveform for an accumulation time; and
 varying the accumulation time for at least one of the tailored waveforms.

3. The method of claim 2 wherein step of varying the accumulation time comprises varying the accumulation time so the subset of ionized molecules attains at least a minimum abundance.

4. The method of claim 2 further comprising the step of normalizing the mass signal resulting in step (c) based on the accumulation time.

5. The method of claim 1 wherein step (a) comprises selecting at least two gaps in frequency space such that the subset of ionized molecules comprises ionized molecules within mass to charge ratio ranges with median values which are substantially the mass-to-charge ratios of the integer charge states of a select ion mass.

6. The method of claim 1 wherein:
step (a) comprises segregating a subset of ionized molecules that are substantially cations; and
step (b) comprises reacting the subset of ionized molecules with an anionic quencher.

7. The method of claim 1 further comprising the step of analyzing by a mass spectrometry technique, the ionized molecules having the highest mass to charge ratio resulting from step (b).

8. The method of claim 1 wherein step (a) comprises:
trapping the plurality of ionized molecules in an ion trap; and
retaining in the ion trap the subset of ionized molecules.

9. An article of manufacture having computer-readable program means for performing the method of claim 1 embodied thereon.

10. A method of analyzing a sample of molecules comprising the steps of:
(a) using a tailored waveform having at least two gaps in frequency space for an accumulation time to segregate a subset of ionized molecules from a plurality of ionized molecules;
(b) reacting the subset of ionized molecules with a quencher for a charge reduction period to reduce the charge state of ionized molecules in the subset of ionized molecules;
(c) determining a mass signal for the ionized molecules having the highest mass to charge ratio resulting from step (b); and
(d) repeating steps (a)–(c) for at least another accumulation time.

11. The method of claim 10 further comprising the step of repeating at least steps (a)–(c) for at least another tailored waveform having a different at least two gaps in frequency space to define a mass spectrum.

12. The method of claim 10 wherein step (d) is repeated so the subset of ionized molecules attains at least a minimum abundance.

13. The method of claim 10 further comprising the step of normalizing the mass signal resulting in step (c) based on the accumulation time.

14. The method of claim 10 wherein step (a) comprises selecting at least two gaps in frequency space such that the subset of ionized molecules comprises ionized molecules within mass to charge ratio ranges with median values which are substantially the mass-to-charge ratios of the integer charge states of a select ion mass.

15. The method of claim 10 wherein:
step (a) comprises segregating a subset of ionized molecules that are substantially cations; and
step (b) comprises reacting the subset of ionized molecules with an anionic quencher.

16. The method of claim 10 further comprising the step of analyzing by a mass spectrometry technique, the ionized molecules having the highest mass to charge ratio resulting from step (b).

17. The method of claim 10 wherein step (a) comprises:
trapping the plurality of ionized molecules in an ion trap; and
retaining in the ion trap the subset of ionized molecules.

18. An article of manufacture having computer-readable program means for performing the method of claim 10 embodied thereon.

19. A method of analyzing a sample of molecules comprising the steps of:
(a) using a primary tailored waveform having at least two gaps in frequency space to segregate a first subset of ionized molecules from a plurality of ionized molecules;
(b) reacting the first subset of ionized molecules with a quencher for a first charge reduction period to reduce the charge state of ionized molecules in the first subset of ionized molecules;
(c) using a secondary tailored waveform having at least one gap in frequency space to segregate a second subset of ionized molecules resulting from step (b);
(d) determining a mass signal for the ionized molecules having the highest mass to charge ratio resulting from step (c); and
(e) repeating steps (a)–(d) for at least another primary tailored waveform having a different at least two gaps in frequency space and at least another secondary tailored waveform having at least one gap in frequency space to define a mass spectrum.

20. The method of claim 19 further comprising the step of reacting the second subset of ionized molecules with a quencher for a second charge reduction period to reduce the charge state of ionized molecules in the second subset of ionized molecules.

21. The method of claim 19 further comprising the steps of:
using at least one of the primary and secondary tailored waveforms for an accumulation time; and
varying the accumulation time for at least one of the another primary and secondary tailored waveforms.

22. The method of claim 21 wherein the step of varying the accumulation time comprises varying the accumulation time so the second subset of ionized molecules attains at least a minimum abundance.

23. The method of claim 21 further comprising the step of normalizing the mass signal resulting in step (d) based on the accumulation time.

24. The method of claim 19 wherein step (a) comprises selecting at least two gaps in frequency space such that the first subset of ionized molecules comprises ionized molecules within mass to charge ratio ranges with median values which are substantially the mass-to-charge ratios of the integer charge states of a select ion mass.

25. The method of claim 19 wherein:
step (a) comprises segregating a subset of ionized molecules that are substantially cations; and
step (b) comprises reacting the subset of ionized molecules with an anionic quencher.

26. The method of claim 19 further comprising the step of analyzing by a mass spectrometry technique, the ionized molecules having the highest mass to charge ratio resulting from step (c).

27. The method of claim 19 wherein step (a) comprises:
trapping the plurality of ionized molecules in an ion trap; and
retaining in the ion trap the subset of ionized molecules.

28. An article of manufacture having computer-readable program means for performing the method of claim 19 embodied thereon.

29. A method of analyzing a sample of molecules comprising the steps of:
(a) using a tailored waveform having at least two gaps in frequency space to segregate a subset of ionized molecules from a plurality of ionized molecules;

(b) reacting the subset of ionized molecules with a quencher for a charge reduction period to reduce the charge state of ionized molecules in the subset of ionized molecules;

(c) detecting the ionized molecules having the highest mass to charge ratio resulting from step (b); and (d) repeating steps (a)–(c) for at least another tailored waveform having a different at least two gaps in frequency space to analyze a sample of molecules.

30. The method of claim 29 further comprising the steps of:

using the tailored waveform for an accumulation time; and varying the accumulation time for at least one of the tailored waveforms.

31. The method of claim 30 wherein the step of varying the accumulation time; and comprises varying the accumulation time so the subset of ionized molecules attains at least a minimum abundance.

32. The method of claim 29 wherein step (a) comprises selecting at step (a) selecting at least two gaps in frequency space such that the subset of ionized molecules comprises ionized molecules within mass to charge ration ranges with median values which are substantially the mass-to-charge ratios of the integer charge states of a select ion mass.

33. The method of claim 29, wherein:

step (a) comprises segregating a subset of ionized molecules that are substantially cations; and step (b) comprises reacting the subset of ionized molecules with an anionic quencher.

34. The method of claim 29, further comprising the step of analyzing by a mass spectrometry technique, the ionized molecules having the highest mass to charge ratio resulting from step (b).

35. The method of claim 29 wherein step (a) comprises:

trapping the plurality of ionized molecules in an ion trap; and retaining in the ion trap the subset of ionized molecules.

36. An article of manufacture having computer-readable program means for performing the method of claim 29 embodied thereon.

37. The method of claim 29 wherein the detecting step is performed using at least one of the group consisting of a channeltron electron multiplier, a discrete dynode electron multiplier, a CCD, electron multiplier, Faraday cup, Daly detector, or a conductive plate electrically connected to an ammeter.

* * * * *